United States Patent [19]

Lenfant et al.

[11] Patent Number: 4,897,351

[45] Date of Patent: Jan. 30, 1990

[54] PROCESS OF SELECTIVE BIOCONVERSION OF ISOSORBITOL DINITRATE

[75] Inventors: Maryse Lenfant; Jacek Ropenga, both of Gif S. Yvette; Eric Wimmer, Ballancourt, all of France

[73] Assignees: Societe National des Poudres et Explosifs; Centre National de la Recherche Scientifique, both of France

[21] Appl. No.: 72,494

[22] Filed: Jul. 13, 1987

[30] Foreign Application Priority Data

Jul. 11, 1986 [FR] France ................................ 86 10177

[51] Int. Cl.[4] ......................... C12P 19/12; C12P 1/66; C12R 1/465

[52] U.S. Cl. .................................... 435/119; 435/193; 435/911; 435/913

[58] Field of Search ................................ 435/119, 193

[56] References Cited

U.S. PATENT DOCUMENTS 4,381,400 4/1983 Emeury et al. ..................... 549/464

OTHER PUBLICATIONS

Chem. Abs. 98-11045t, Down et al., vol. 98-1983, Nitrates: Cardiovasc: Eff. 1981, pp. 110"116.
Chem. Abs. 107-76009h, Ropenga et al., App. Microbio. Biotech, 1987, 26(2), 117-119, Jour. of Pharm. Sci., vol. 63#7, 1974, pp. 1147-1149, Down et al.
Chem. Abs. 101-#3, Jul. 1984, p. 17, 16774v, King et al.

*Primary Examiner*—Herbert J. Lilling
*Attorney, Agent, or Firm*—Pollock, Vande Sande & Priddy

[57] ABSTRACT

The invention relates to a process of selective bioconversion of DINIS into MONIS-5, wherein the DINIS is added to a medium containing at least one microorganism possessing a glutathion transferase or an acellular extract of such a microorganism.

9 Claims, No Drawings

PROCESS OF SELECTIVE BIOCONVERSION OF ISOSORBITOL DINITRATE

The present invention relates to the selective bioconversion of nitric ester functions into hydroxy functions of the dinitrate of isosorbitol (DINIS).

Distinction is made between two mononitrates of isosorbitol which are named MONIS. When the hydroxy function is in exo position, the compound is named MONIS-5, and when this function is in the endo position, MONIS-2. These two compounds may be represented as follows:

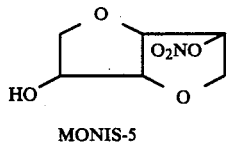  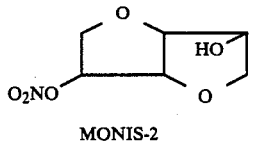

MONIS-5  MONIS-2

The MONIS are known as coronary vasodilators after the fashion of the dinitrate of isosorbitol (DINIS) and of nitroglycerin.

The MONIS are prepared at present by processes which have drawbacks. Synthesis by nitration of isosorbitol requires the use of a nitration mixture $HNO_3$—acetic anhydride—acetic acid which can lead to the formation of acetyl nitrate considered as an explosive more sensitive than nitroglycerin.

Another process consists of preparing the acetates of isosorbitol and then nitrating them; here again, the risks of explosion are considerable, the process long and the yield low.

Novel processes have enabled the risks to be limited in the preparation of this type of compound but without however being fully satisfactory from the point of view of safety and/or yield, as will be seen from French patent 2 500 835.

This is why gentle techniques of preparing these compounds employing bioconversions have great interest.

The process according to the present invention is more particularly intended for the selective bioconversion of DINIS to MONIS-5, and is characterized in that the DINIS is added to a medium containing at least one microorganism possessing a glutathion transferase or an acellular extract of such a microorganism, preferably also the medium involved will be a culture medium for the microorganism.

Among the microorganisms usable within the scope of the present invention, must be mentioned more particularly the protozoa, fungi and bacteria. Among the protozoa, must be mentioned more particularly Tetrahymena, and among the fungi, must be mentioned more particularly Beauveria, Aspergillus, Streptomyces and Cunninghamella.

The fermentation of these microorganisms in a medium containing DINIS leads to the formation of MONIS, with a preponderance of MONIS-5 with respect to MONIS-2.

Although the bioconversion of DINIS may be effected in a medium only containing microorganism cells, it is preferable to effect this bioconversion in a culture medium. This culture medium will, preferably, be a minium medium containing, preferably, 5 to 20 g/l of glucose, yeast extracts, and the bioconversion will be carried out at a temperature of the order of 20° to 30° C. at a pH close to neutrality.

Experiments carried out have enabled it to be shown that the addition of amino acids to the culture medium increased distinctly the yield of MONIS-5.

Under the preceding conditions, a concentration of a DINIS comprised between 1 and 5 g/l is utilisable.

It is, in addition, preferable to use, when it is possible for the fungis, an already aged mycelium which gives higher bioconversion yields. Of course, when a growth medium is used, it is necessary to provide for aeration of the medium.

As has been previously indicated, it is also possible to provide for the use of the mycelium in a medium which is not a growth medium; it is even possible to use, in certain cases, extracts partly freed from a cellular structure, this facilitating the subsequent separating operations.

In certain cases, the microorganisms could be used in immobilized form, for example by absorption on a support or by encapsulation in a polymer, agar for example.

The conditions of practicing this bioconversion enables any risk associated with manipulation of this type of product to be avoided and enable yields of MONIS-5 to be obtained which are very considerable, as will emerge from the following examples.

The DINIS used within the scope of the present invention by way of starting material is an explosive substance, but it is possible to handle it with complete safety to the extent that this substance is moist or impregnated with solvent or in solution.

The following examples are intended to demonstrate other advantages and features of the present invention.

EXAMPLE 1

Bioconversion of DINIS by cultures of *Cunninghemella echinulata* (*C. ech.*) NRRL 3655 and *Cunninghamella elegans* (*C. el.*) ATCC 3245

The precultures were made in an inclined agar tube, at 24° on potato gelose (I.P.P.). The cultures (50 ml) were grown in "soya flour" liquid medium in Erlenmeyer flasks of 250 ml, shaken (180 rpm.) at 24° C. The seedings were preformed by the addition of 0.5 to 1 ml of a suspension of spores at the average density of $3.10^5$ spores/ml. After 44 hours of growth, and according to the test, the DINIS was added either to the culture, or to the mycelium suspension in phosphate buffer 0.05M pH 7, and incubated at 24° C. for selected periods of time.

Various conditions of biotransformation were studied:

a) Incubation in a culture medium, the DINIS is added at 1 g/l in solution in methanol (50 mg/ml).

b) Incubation in phosphate buffer 0.05M pH 7, the DINIS is added at 1 g/l in solution in methanol (50 mg/ml).

c) Incubation in phosphate buffer 0.05M pH 7, the DINIS is added in powder at 1 g/l.

The amounts of MONIS-5 and MONIS-2 formed in the course of time by bioconversion, were estimated by analysis by HPLC on a μBondapack C-18 column.

The results obtained are collected for *C. ech.* in Table 1 and for *C. el.* in Table 2.

TABLE 1

Biotransformation of DINIS by Cunninghamella echinulata NRRL 3655 (ATCC 36190)

(a) Incubation in culture medium; DINIS 1 g/l in methanol (50 mg/ml); age of the cultures 44 hours; amount of mycelium: 73 g/l;

| Hours | | 4 | 8 | 21 | 28 | 33 | 46 | 55 | 73 | 100 |
|---|---|---|---|---|---|---|---|---|---|---|
| DINIS | (mg/l) | 595 | 570 | 535 | 473 | 445 | 351 | 339 | 262 | 182 |
| MONIS-2 | (mg/l) | 8 | 26 | 56 | 66 | 73 | 83 | 100 | 104 | 103 |
| MONIS-5 | (mg/l) | 27 | 64 | 134 | 175 | 186 | 232 | 239 | 268 | 197 |

(b) Incubation in phosphate buffer 0.05 M, pH 7; DINIS 1 g/l in methanol (50 mg/l); age of cultures 44 hours; amount of mycelium: 80 g/l;

| Hours | | 4 | 8 | 21 | 33 | 46 | 73 | 120 |
|---|---|---|---|---|---|---|---|---|
| DINIS | (mg/l) | 507 | 655 | 442 | 443 | 394 | 328 | 272 |
| MONIS-2 | (mg/l) | 10 | 24 | 27 | 62 | 76 | 83 | 103 |
| MONIS-5 | (mg/l) | 26 | 51 | 108 | 148 | 198 | 209 | 227 |

(c) Incubation in phosphate buffer 0.05 M, pH 7; DINIS 1 g/l in powder; age of the cultures 44 hours; amount of mycelium 101 g/l;

| Hours | | 8 | 21 | 33 | 46 | 73 |
|---|---|---|---|---|---|---|
| DINIS | (mg/l) | 605 | 533 | 510 | 480 | 406 |
| MONIS-2 | (mg/l) | 15 | 42 | 48 | 56 | 82 |
| MONIS-5 | (mg/l) | 30 | 64 | 101 | 136 | 145 |

Initial concentration of DINIS: The concentrations evaluated in DINIS, MONIS-2 and MONIS-5 are not corrected. (An evaporation of the order of 10 to 15% must be taken into account).

TABLE 2

Biotransformation of DINIS by Cunninghamella elegans (ATCC 9245)

(a) Incubation in culture medium; DINIS 1 g/l in methanol (50 mg/ml); age of the cultures: 44 hours; amount of mycelium: 73 g/l;

| | | Hours | | | | | | |
|---|---|---|---|---|---|---|---|---|
| | | 4 | 21 | 33 | 46 | 55 | 73 | 120 |
| DINIS | (mg/l) | 678 | 545 | 441 | 242 | 265 | 123 | 14,5 |
| MONIS-2 | (mg/l) | 18 | 112 | 165 | 185 | 314 | 305 | 170 |
| MONIS-5 | (mg/l) | 26 | 99 | 121 | 160 | 214 | 230 | 188 |

(b) Incubation in a phosphate buffer 0.05 M, pH 7; DINIS 1 g/l in methanol (50 mg/ml); age of the cultures: 44 hours; amount of mycelium: 80 g/l;

| | | Hours | | | | | |
|---|---|---|---|---|---|---|---|
| | | 4 | 8 | 21 | 33 | 46 | 73 |
| DINIS | (mg/l) | 631 | 625 | 517 | 463 | 344 | 325 |
| MONIS-2 | (mg/l) | 13 | 19 | 63 | 98 | 115 | 149 |
| MONIS-5 | (mg/l) | 23 | 32 | 71 | 102 | 115 | 126 |

Initial concentration of DINIS: The concentrations evaluated in DINIS, MONIS-2 and MONIS-5 are not corrected. (An evaporation of the order of 10 to 15% must be taken into account.

1. The two strains C. ech. and C. el. convert the DINIS into MONIS-5 and MONIS-2.

2. The best conversion ratio is observed when the strain C. ech. is incubated in a culture medium for 73 hours. An extended incubation time leads to the drop of the total yield (DINIS+MONIS-5+MONIS-2) apparently by subsequent conversion of mononitrated derivatives into isosorbide.

Under these conditions, the mixture DINIS, MONIS-5, MONIS-2 is obtained with a total yield of 58%. The mononitrated derivatives are formed with respective yields of 33% of MONIS-5 and 13% approximately of MONIS-2 (yield calculated on the amount of DINIS consumed), namely a ratio:

$$\frac{MONIS-5}{MONIS-2} = 2.6$$

In order to improve the conversion yields, tests were carried out on an amount of DINIS reduced to 500 mg/l; the results obtained are collected in Table 3 below:

TABLE 3

Biotransformation of DINIS by Cunninghamella echinulata NRRL 3655 (ATCC 36190)

| Hours | Test | 48 | 69 | 93 | 116 | 140 |
|---|---|---|---|---|---|---|
| DINIS (mg/l)* | 1 | 268 | 169 | 107 | 68 | 60 |
| | 2 | 270 | 169 | 116 | 86 | 75 |
| MONIS-5 (mg/l)* | 1 | 143 | 190 | 216 | 218 | 244 |
| | 2 | 150 | 197 | 219 | 225 | 238 |
| MONIS-2 (mg/l)* | 1 | 61 | 67 | 95 | 71 | 93 |
| | 2 | 58 | 89 | 98 | 106 | 96 |

DINIS 500 mg/l in methanol (50 mg/ml); incubation in culture medium; age of the cultures: 44 hours; average amount of mycelium: 78 g/l;

*The concentrations evaluated in DINIS, MONIS-5 and MONIS-2 are not corrected. (Evaporation of the order of 10 to 15% must be taken into account).

Under these conditions, it is possible to obtain, for incubation periods varying from 63 to 93 hours, the mixture (DINIS+MONIS-5+MONIS-2) with an overall yield of 80–90%. The mononitrated derivatives MONIS-5 and MONIS-2 are formed with respective yields of 50 and 22% (calculated on the amount of DINIS consumed).

Contrary to strain C. ech. which leads to the preferential formation of MONIS-5, the strain C. el. performs the conversion of the DINIS preferentially into isomer 2.

These results indicate that in a same family of Phycomycetes, the different strains can contain, in variable proportions, enzymes which specifically must enable the conversion of the DINIS into each of the isomers MONIS-5 and MONIS-2.

EXAMPLE 2

Mutagenesis trials of *Cunninghamella echinulata*

Development of a mutagenesis with aziridine (ethyleneimine)

After various attempts, it has appeared that the treatment of C. ech. spores for 4 minutes with a lethal solution of 5% aziridine induced the formation of mutants detectible after 72 hours of incubation on gelose.

Mutagenesis conditions

The spores of *C. ech.* sampled from 2 inclined tubes of pre-cultures were washed with 8 ml of water (4 ml/tube) and resuspended in 4.75 ml of water to which 0.25 ml of aziridine (final solution 5%) were added.

After 4 minutes specimens (0.5 ml) were taken up, diluted ($10^2$, $10^3$, $10^4$ times) then seeded on Petri dishes of potato gelose in the proportion of 0.2 ml/dish.

The results obtained show that:

1. The concentration in spores of the solution before treatment was $2 \times 10^5$ spores/ml and $3 \times 10^3$ spores/ml (1.5%) after treatment.

2. Possibility of isolating muted strains after 72 hours of cultures.

The effectiveness of the mutants isolated to effect the biotransformation of the DINIS was evaluated in a liquid medium under conventional conditions.

Results 15 mutants were isolated and cultivated on inclined agar. The mutants were evaluated for their capacity to biotransform DINIS, under the conditions selected for *C. ech.* (44-hour mycelium). The biotransformation was evaluated after 48 hours of incubation.

It appears:

1. That it is possible to vary in the strains, by mutagenesis, the proportion of bioconversion of MONIS-2 and MONIS-5 such that the ratio MONIS-5/MONIS-2 varies from 2.07 to 2.91, hence the ratio of the enzymes responsible for the bioconversion.

2. That 2 mutants are more effective than the initial strain to obtain preferentially the MONIS-5 from DINIS, a mutant resulting preferentially in isomer 2.

3. That two mutants effect the bioconversion with a quantitative overall yield (DINIS+MONIS-5+MONIS-2)

EXAMPLE 3

Bioconversion of DINIS by various strains of Beauveria, Aspergillus and Streptomyces The following experiments were carried out with various fungi. These were:
Beauveria bassiana ATCC 7159
Aspergillus ochraceus ATCC 18500
Aspergillus foetidus ATCC 10254
Aspergillus allicaeus ATCC 10060
Aspergillus niger ATCC 9142
Stroptomyces Tü 96
Streptomyces incarnatus.

The preliminary experiments which are reported were made under the conditions used for *C. ech.* (Example 1).

The precultures were carried out on inclined potato gelose. The cultures were grown in a "soya flour" liquid medium for 48 hours. The DINIS was added (500 mg/l) to the culture medium and incubated for 44 and 68 hours. The bioconversion ratios were obtained by determination by HPLC.

The results obtained (Table 4) indicate that:

1. All the strains studied performed the conversion of the DINIS into MONIS-5 and MONIS-2 in variable proportions and at variable speeds.

2. The *Beauveria bassiana* ATCC 7159 strain is noteworthy; it results after 48 hours of incubation in a complete and quantitative conversion of the DINIS into MONIS-5 and MONIS-2 with respective yields of 85 and 15%.

TABLE 4

Biotransformation of DINIS by different strains of fungi

| Strain | Duration of incubation (hour) | Amount of substance | | |
|---|---|---|---|---|
| | | MONIS-2 | MONIS-5 | DINIS |
| Beauveria bassiana ATCC 7159 | 44 | 46 | 252 | 110 |
| | 68 | 66 | 361 | 0 |
| Aspergillus foetidus ATCC 10254 | 44 | 18 | 31 | 430 |
| | 68 | 23 | 38 | 425 |
| Aspergillus alliaiens ATCC 10060 | 44 | 60 | 71 | 286 |
| | 68 | 61 | 97 | 212 |
| Aspergillus niger ATCC 9142 | 44 | 0 | 43 | 383 |
| | 68 | 10 | 58 | 377 |
| Aspergillus ochraceus ATCC 18500 | 44 | 0 | 27 | 396 |
| | 68 | 0 | 38 | 373 |
| Streptomyces Tu 96 | 44 | 0 | 21 | 497 |
| | 68 | 28 | 47 | 413 |
| Streptomyces iscariatus | 44 | 20 | 70 | 400 |
| | 68 | 53 | 100 | 360 |

The DINIS (500 mg/ml) was added to the culture after 48 hours of growth. The evaluation of the yield takes into account the loss of the $NO_2$ group during the conversion DINIS (MW 236) into MONIS (MW 191).

EXAMPLE 4

1) Culture conditions of the strain *Beauveria bassiana* (ATCC 7159)

1.1) Pre-cultures

The pre-cultures were carried out at 24° C. over 6 days in an agar tube on 2 media at choice:
potato gelose (I.P.P.);
$M_2$ medium constituted of "Bacto Yeast extract" 4 g, "Bacto Malt extract" 10 g, "Bacto Dextrose" 4 g, agar 20 g per 1 liter of water, pH 7, according to E. B. Shirling and D. Gottlieb (Intern. J. Syst. Bact. 16, 313–340, 1966).

A more abundant sporulation is observed on $M_2$ medium.

1.2) Cultures

The cultures of *B. bassiana* (B. b.) were carried out in "soya flour" liquid medium according to R. E. Betts, D. E. Walters, J. P. Rossaza (J. Med. Chem. 17, 597–602, 1974), constituted by soya flour 5 g, glucose 20 g. "Yeast extract" 5 g, NaCl 5 g, $K_2HPO_4$ 5 g, mineral salts $Fe^{+2}$ 0.1 mg/l, $Zn^{+2}$ 0.1 mg/l, $Mo^{+2}$ 0.01 mg/l, $Cu^{+2}$ 0.02 mg/l, $Mn^{+2}$ 0.01 mg/l, water at pH 7.

50 ml medium was seeded with 0.5 to 1 ml of a spore suspension 500 000 to 300 000 spores/ml) prepared from an agar tube taken up again with 6 ml of distilled water. The cultures carried out in Erlenmeyer flasks of 250 ml were shaken on a rotary shaker at 180 rpm at 24° C.

2) Analysis of the biotransformation products

The relative concentrations of DINIS, MONIS-5 and MONIS-2 were evaluated at HPLC.

Analysis was carried out on a Waters apparatus equipped with a U.V. detector (Pye Unicam) and a Waters integrater.
μBondapack C18 (10 μm-4×250 mm) column
solvent MeOH/$H_2O$:25/75
flow rate 0.5 ml/min.
U.V. detector $\lambda = 220$ nm, sensitivity 0.08/5.

The separation of the 3 compounds is satisfactory:
MONIS-5:Rt=10 min 20 sec
MONIS-2:Rt=9 min
DINIS:Rt=25 min 20 sec The very great sensitivity of the technique enables the evaluation of amounts of substances of the order of 60 ng (3 mg/l) to 6 μg (300 mg/l) per 20 μg injected, hence concentrations compatible with the conditions used in the bioconversion trials. The linear response obtained for the three compounds between the surface of the peaks and the amounts of substances injected enables the evaluation of the concentrations of the different constituents present in the incubation medium.

3) Extraction of the constituents from the culture medium 0.5 ml of culture medium after filtration (or centrifugation) of the mycelium is placed on a glass column (diameter of 0.5 cm) filled with 1 g of Kieselgel 60 silica. 10 ml of ethyl ether were passed through. The ether was evaporated to dryness under vaccuum, and the sample was diluted with 2 ml of the mixture $MeOH/H_2O$ (25/75). This solution was injected directly into an HPLC apparatus. The extraction was quantitative.

4) Study of the bioconversion conditions of the DINIS by *Beauveria bassiana*

Studies were carried out systematically on cultures of 50 ml in volume, aged 48 hours, the DINIS was added in solution in methanol at 50 mg/ml.

4.1) Incubation in a culture medium:importance of the concentration of the DINIS (0.5 and 1 g/l)

The bioconversion was evaluated between 17 and 45 hours of incubation, the results obtained with a concentration of DINIS at 0.5 g/l (Table 5) indicate an almost complete bioconversion from 25 hours (residual amount of DINIS 3%), and total at 38 hours, which leads to the formation of the mixture MONIS-5 (85%) and MONIS-2 (15%), namely a ratio MONIS-5/MONIS-2=5.16/1, with a yield of 93%.

TABLE 5

Biotransformation of DINIS by Beauveria bassiana ATCC 7159

| Time (hour) | Amount of substance MONIS-5 | MONIS-2 | DINIS |
|---|---|---|---|
| 17 | 108 | 33 | 361 |
| 18 | 190 | 48 | 304 |
| 25 | 307 | 62 | 15 |
| 38 | 315 | 61 | 0 |
| 45 | 290 | 59 | 0 |

Incubation of B. bassiana in culture medium. Concentration of the DINIS: 500 mg/ml.

When the concentration of DINIS is brought to 1 g/l for the same amount of Mycelium (Table 6), 68 hours of incubation are necessary to observe complete consumtion of the DINIS, formation of the MONIS-2, MONIS- is effected with an overall yield of 91%. However this slower bioconversion leads to the mixture MONIS-5/MONIS-2=3.9/1, hence less favorable to the production of the isomer 5.

TABLE 6

Biotransformation of DINIS by Beauveria bassiana ATCC 7159

| Time (hour) | Amount of substance MONIS-5 | MONIS-2 | DINIS |
|---|---|---|---|
| 17 | 91 | 41 | 851 |
| 45 | 449 | 138 | 438 |
| 68 | 588 | 150 | 0 |

Incubation of B. bassiana in a culture medium. Concentration of the DINIS: 1 g/l The importance of the ratio amount of DINIS/amount of mycelium for the selectivity of the biotransformation is illustrated by these experiments.

4.2) Incubation in water

A second series of experiments was performed in water. These conditions should permit a simplified extraction of the bioconversion products from the incubation medium devoid of the constituents of the culture medium.

A mycelium obtained from a 48 hour culture was suspended in water in the presence of a methanol solution of DINIS at the final concentration of 1 g/l.

Analysis of the bioconversion medium (Table 7) shows that under these conditions *B. bassiana* very slowly hydrolyzes DINIS. After 30 hours incubation, 40% of DINIS is still present in the medium.

TABLE 7

Biotransformation of DINIS by Beauveria bassiana ATCC 7159

| Time (hour) | Amount of substance MONIS-5 | MONIS-2 | DINIS |
|---|---|---|---|
| 17 | 48 | 21 | 987 |
| 45 | 171 | 44 | 767 |
| 68 | 330 | 91 | 600 |
| 90 | 432 | 100 | 10 |

Incubation of B. bassiana in water. DINIS: 1 g/l

We claim:

1. A process of selective bioconversion of dinitrate of isosorbitol (DINIS) into exo mononitrate of isosorbitol (MONIS-5) having the formula 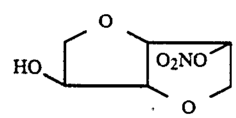 wherein said DINIS is provided in a culture medium containing at least one microorganism possessing a glutathion transferase or an acellular extract of such a microorganism.

2. A process according to claim 1, wherein the DINIS is placed in a culture medium containing a microorganism possessing a glutathion transferase.

3. A process according to claim 1, wherein the microorganism is selected from among protozoa, fungi and bacteria.

4. A process according to claim 3, wherein the microorganism is selected from the types: Tetrahymena, Cunninghamella, Aspergillus, Beauveria and Streptomyces.

5. A process according to claim 1, wherein the microorganism is selected from the genus Beauveria.

6. A process according to claim 1, wherein the bioconversion is carried out at a temperature of the order of 20° to 30° C.

7. A process according to claim 1, wherein the medium is a minimum culture containing from 5 to 20 g/l of glucose and a source of organic nitrogen containing amino acids.

8. A process according to claim 1, wherein the DINIS is provided in a concentration of 1 to 5 g/l of medium.

9. A process according to claim 1, wherein the pH of the medium is close to neutrality.

* * * * *